(12) United States Patent
Andreu et al.

(10) Patent No.: US 12,179,027 B2
(45) Date of Patent: Dec. 31, 2024

(54) ACTIVE IMPLANTABLE MEDICAL DEVICE

(71) Applicants: NEURINNOV, Montpellier (FR); CENTRE NATIONAL DE LA RECHERCHE SCIENTIFIQUE, Paris (FR); INRIA—INSTITUT NATIONAL DE RECHERCHE EN INFORMATIQUE ET EN AUTOMATIQUE, Le Chesnay (FR); UNIVERSITÉ DE MONTPELLIER, Montpellier (FR)

(72) Inventors: David Andreu, Montarnaud (FR); David Guiraud, Montpellier (FR); Brice Sorli, Montagnac (FR); Arnaud Vena, Saint-Mathieu-de-Tréviers (FR)

(73) Assignees: NEURINNOV, Montpellier (FR); CENTRE NATIONAL DE LA RECHERCHE SCIENTIFIQUE, Paris (FR); INRIA—INSTITUT NATIONAL DE RECHERCHE EN INFORMATIQUE ET EN AUTOMATIQUE, Le Chesnay (FR); UNIVERSITÉ DE MONTPELLIER, Montpellier (FR)

( * ) Notice: Subject to any disclaimer, the term of this patent is extended or adjusted under 35 U.S.C. 154(b) by 131 days.

(21) Appl. No.: 18/246,601

(22) PCT Filed: Sep. 24, 2021

(86) PCT No.: PCT/FR2021/051643
§ 371 (c)(1),
(2) Date: Mar. 24, 2023

(87) PCT Pub. No.: WO2022/064153
PCT Pub. Date: Mar. 31, 2022

(65) Prior Publication Data
US 2023/0364431 A1    Nov. 16, 2023

(30) Foreign Application Priority Data

Sep. 25, 2020  (FR) ..................................... 2009787

(51) Int. Cl.
*A61N 1/37* (2006.01)
*A61N 1/372* (2006.01)
(Continued)

(52) U.S. Cl.
CPC ........ *A61N 1/37229* (2013.01); *A61N 1/375* (2013.01); *A61N 1/3787* (2013.01)

(58) Field of Classification Search
CPC . H01Q 1/24; H01Q 1/22; H01Q 1/273; A61N 1/37223–37229; A61N 1/375; A61N 1/378
See application file for complete search history.

(56) References Cited

U.S. PATENT DOCUMENTS 6,539,253 B2 * 3/2003 Thompson ......... A61N 1/37229
607/2
11,490,813 B2 * 11/2022 Park ...................... H01Q 1/244
(Continued)

FOREIGN PATENT DOCUMENTS

FR    3085551 A1    3/2020

OTHER PUBLICATIONS

International Search Report mailed Jan. 24, 2022, in International Application No. PCT/FR2021/051643, 5 pages.

*Primary Examiner* — Hasan Islam
(74) *Attorney, Agent, or Firm* — Maier & Maier, PLLC

(57) ABSTRACT

An active implantable medical device including, once implanted, a module external to the patient and a module inside the patient, the external module and the internal module being intended to transfer energy and data from one to the other. Also, a method for transferring energy and data, (Continued)

the method being implemented by the active implantable medical device.

14 Claims, 2 Drawing Sheets

(51) Int. Cl.
  *A61N 1/375* (2006.01)
  *A61N 1/378* (2006.01)

(56) References Cited

U.S. PATENT DOCUMENTS

| | | |
|---|---|---|
| 2014/0002314 A1* | 1/2014 | Li ............................ H01Q 1/24 343/702 |
| 2015/0209591 A1 | 7/2015 | Meskens |
| 2018/0034319 A1 | 2/2018 | Robert |

* cited by examiner

ACTIVE IMPLANTABLE MEDICAL DEVICE

FIELD

The present invention relates to medical devices, more specifically active implantable medical devices (AIMD).

BACKGROUND

In a conventional and well-known in manner, an active implantable medical device (AIMD) is defined as a device the operation of which depends on a source of energy other than that generated by the human body, and which acts on this energy supplied by modifying the density or by converting it. An AIMD may be intended to be partially or completely inserted into the human body, so as to restore a vital function, compensate for a deficiency and/or measure physiological parameters. Conventionally, an AIMD thus comprises at least one active element intended to be partially inserted into the human body by clinical intervention and intended to remain in place after the procedure for at least 30 days. In a broad sense, it is considered that an AIMD allows transferring energy and information on both sides of the skin of an implanted patient. It is known from the prior art that the best option, currently, for managing the transfer of energy and/or information from the implants, is the WPT (wireless power transfer) option based on electromagnetic field transfers. Thus, most implanted devices include two coils, the first one located outside the body of an implanted subject and the second one located inside the body of the implanted subject. Hence, this transfer is performed by (inductive) wireless link, through the skin and in near-field, more particularly via the NFC technology (HF at 13.56 MHz, according to the standards ISO 14443 or ISO 15693). The NFC technology allows reducing the size of the coils. The acronym "NFC" stands for "Near-Field Communication" and has its equivalent acronym in French: "CCP" standing for "communication en champ proche". It consists of a short-range and high-frequency wireless communication technology. This technology, well-known per se, enables the exchange of information between peripherals, usually an NFC chip and an NFC reader, up to a distance of about 10 cm. This technology is an extension of the standard ISO/CEI 14443 standardising proximity cards using radio-identification (RFID) which combine a smart card and a reader within a single peripheral. In a manner known from the prior art, NFC chips are in particular composed of an antenna and an integrated circuit and have an input stage containing a protection circuit (including in particular at least one Zener diode) intended to protect the NFC chip, and therefore leading to limiting the voltage developed in the antenna. As known from the prior art, this intrinsic characteristic of NFC chips limits the energy recoverable by other functional elements of the implant. Indeed, the intrinsic limitation of the technology is that the NFC chip, passive in this case, returns little of the energy received thereby, resulting in a very low efficiency (about 15 mW recovered for 500 mW emitted).

These observations may apply to any form of chip including an antenna intended to receive energy and/or information.

In addition, in the particular context of an implantable device, the transfer of energy and/or information is strongly attenuated by the tissues of the person equipped with the device. This attenuation leads to several constraints. On the one hand, the emitted signals should have enough intensity to be properly received by the receiver. On the other hand, the transfer of energy should be limited so as not to damage the tissues—in accordance with the specific absorption rate (SAR) regulatory limits. This trade-off is poorly taken into account in the prior art.

The objective of the invention is to transmit energy and data via an inductive link to a device implanted in the body, from an external device by optimising the recovered energy while controlling the range of the implant.

The present invention achieves the aforementioned objective by proposing the addition of an electronic assembly including an antenna associated with an internal circuit, which may be an NFC chip, to allow reaching a voltage developed by the receiver antenna beyond limits imposed by the internal circuit.

SUMMARY

Hence, the invention relates to an active implantable medical device able to be partially implanted in a subject, the device comprising, once implanted, an external module outside to the subject and an internal module inside the subject, the external module and the internal module being intended to transfer data from one to the other and energy from the external module to the internal module,
the external module including an external antenna,
the internal module including:
an internal antenna defining two terminals;
an association in series between said terminals of an internal integrated circuit associated with the internal antenna having an equivalent input impedance with a capacitive part C4 and a capacitor with a capacitance C3 with the ratio $$\frac{C_3}{C_3 + C_4}$$

greater than or equal to 0.1, and
an electrical energy recovery electronic assembly connected to said terminals, the recovery electronic assembly being external to the internal integrated circuit.

Thus, this solution allows achieving the aforementioned objective. In particular, the invention allows transmitting energy and data to a device implanted in the body via a transcutaneous link based on a technology comprising an antenna associated with an integrated circuit, such as the NFC technology, the invention allowing matching the impedance of the integrated circuit (and of the associated antenna) so as to optimise the recovered energy. Thus, this impedance matching is based on the addition of an electronic assembly to the integrated circuit (for example that of an NFC chip) to enable the associated antenna to reach a voltage beyond the limits imposed by the integrated circuit and to optimise the efficiency of the energy transfer between the external module and the internal module of the device.

The device according to the invention may comprise one or more of the following features, considered separately from each other or in combination with each other:
the ratio $$\frac{C_3}{C_3 + C_4}$$

is greater than or equal to 0.25, preferably comprised between 0.3 and 0.6

- the external module includes a unique external antenna, and in that the internal module includes a unique internal antenna,
- each antenna is connected to an impedance matching circuit and that each antenna and its associated impedance matching circuit resonate at a frequency comprised between 12 and 14 MHz, more specifically 13.56 MHz,
- the external module and the internal module are intended to transfer energy and data from one to the other simultaneously,
- the external module and the internal module are intended to transfer data from one to the other in a bidirectional manner,
- the external module and the internal module are intended to transfer energy and data from one to the other over a unique frequency band.

The invention also relates to a method for transferring energy and data, the method being implemented by means of a device according to any of the features set out hereinabove, the voltage supplied to the internal integrated circuit being comprised between 100 mV and 5 V, the voltage supplied to the energy recovery electronic assembly being comprised between 100 mV and 50 V.

The method according to the invention may comprise one or more of the following features, considered separately from each other or in combination with each other:

- the transfer rate between the external module and the internal module is comprised between 6 kbit/s and 900 kbit/s, preferably between 106 kbit/s/s and 847 kbit/s or between 6.62 kbit/s and 26.48 kbit/s,
- the efficiency of energy transfer between the external module and the internal module is comprised between 10% and 70%,
- the transfer rate between the external module and the internal module is comprised between 6 kbit/s and 900 kbit/s, preferably between 106 kbit/s and 847 kbit/s or between 6.62 kbit/s and 26.48 kbit/s and in that the efficiency of energy transfer between the external module and the internal module is comprised between 10% and 70%.

DETAILED DESCRIPTION

Figure 1:
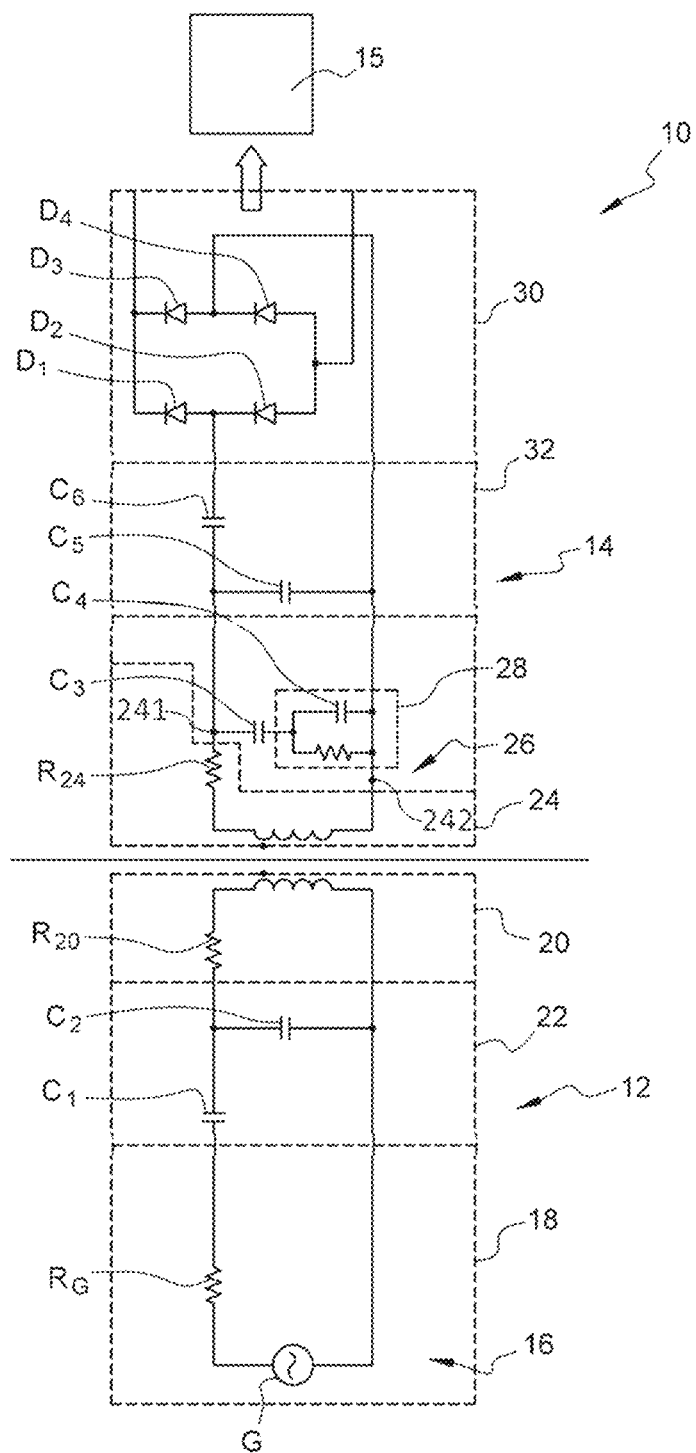
FIG. 1 is an electronic diagram of a device according to the present invention.

Hence, the present invention relates to an active implantable medical device (AIMD) 10, more particularly an inductive link for AIMD 10, able to be partially implanted in a subject, as schematically illustrated in FIG. 1. More particularly, the device 10 comprises two communication and energy transfer modules 12, 14 complementary to each other (an external module 12 and an internal module 14) and a stimulator 15. Instead of a stimulator, some embodiments may, for example, have a device for measuring physiological or physical signals internal to the human body, among which the EMG (electromyogram), the EEG (electroencephalogram), the ECG (electrocardiogram), or ENG (electroneurogram) or temperature measurement.

When the device 10 is implemented for the subject, the external module 12 is positioned outside the subject, for example attached on the skin of the subject, and the internal module 14 is implanted inside the subject, for example under the skin of the subject. The stimulator 15 is connected to the internal module 14 and therefore, after implantation, is also positioned inside the subject. In the embodiment including a stimulator 15, this stimulator 15 may be intended to stimulate tissues, nerves or muscles for example, in order to control organs or movements of limbs of the body.

The external module 12 and the internal module 14 are intended to transfer energy and data from one to the other. Afterwards, the energy is transferred to the stimulator 15. More particularly, the energy transfer is done in a unidirectional manner from the external module 12 to the internal module 14, and the data transfer may be bidirectional, from the external module 12 to the internal module 14 and vice versa.

According to the embodiment illustrated in FIG. 1, the external module 12 is an NFC reader 16 comprising:

- a generator 18 modelled, in FIG. 1, by a sinusoidal generator G with a frequency of 13.56 MHz and the associated resistor $R_G$,
- an external antenna 20 (and associated resistor $R_{20}$) connected to the generator 18,
- an external impedance matching network 22 located between the generator 18 of the NFC reader 16 and the external antenna 20, the external impedance matching network 22 including a first capacitor with a capacitance $C_1$ and a second capacitor with a capacitance $C_2$ connected so as to form a capacitive divider bridge.

Figure 2:
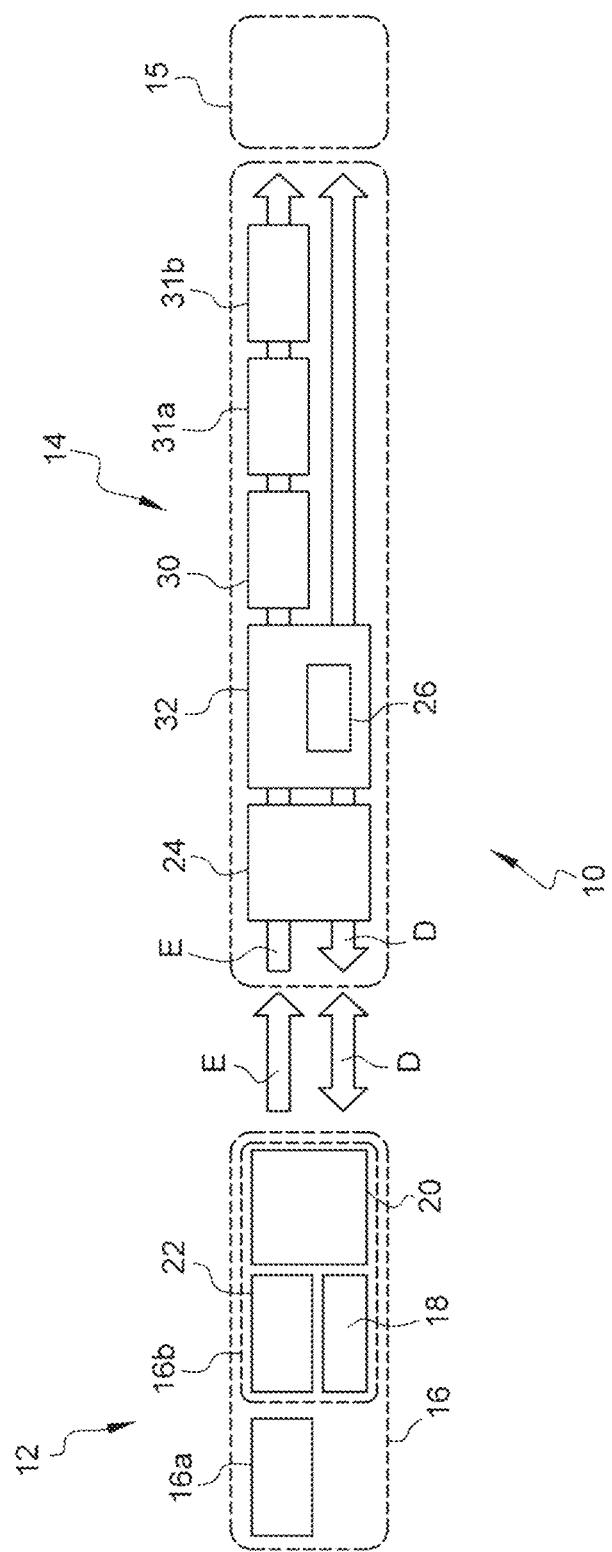
FIG. 2 is a block diagram of a device according to the present invention.

As illustrated in FIG. 2, the generator 18, the external antenna 20 and the external impedance matching network 22 form the analog portion 16b of the NFC reader 16. Furthermore, the NFC reader 16 may comprise a digital portion 16a linked to the analog part 16b by a digital-to-analog converter.

The use of an NFC reader enables data exchange in two directions. The exchanged data include:

- stimulation orders and parameters from the external module 12 to the internal module 14,
- replies, error notifications and measured data returned from the internal module 14 to the external module 12.

In a manner well known per se, impedance matching is a technique for optimising the transfer of an electrical power between an emitter and an electrical receiver to optimise the exchange of data and/or energy between the receiver and the emitter, including the exchange of telecommunications signals.

The internal module 14 comprises:

- an internal antenna 24 (and the associated resistor $R_{24}$) defining two terminals (241, 242),
- a chip 26 intended to cooperate with the NFC reader 16 of the external module 12, the chip 26 being connected to the internal antenna 24, the chip 26 also including the association in series between the terminals 241 and 242 of the internal antenna 24:
  - a third capacitor with a capacitance $C_3$ and
  - an internal integrated circuit 28 having an equivalent input impedance Z whose capacitive portion is modelled by a fourth capacitor with a capacitance $C_4$, and, the ratio $$\frac{C_3}{C_3 + C_4}$$

being greater than or equal to 0.1, $C_3$ and $C_4$ forming a capacitive divider bridge, an electrical energy recovery electronic assembly (not referenced) connected to the internal antenna 24 and intended to supply the simulator 15 with electrical energy, the recovery electronic circuit being external to the internal integrated circuit 28 of the chip 26, the energy recovery electronic circuit including a rectifier circuit 30 located upstream of an energy storage electronic circuit and a voltage regulation circuit (not represented), the rectifier circuit 30 including several diodes $D_1$, $D_2$, $D_3$, $D_4$ intended to generate a DC voltage source intended to power the energy recovery electronic assembly, an impedance matching internal network 32 located between the internal antenna 24 and the rectifier circuit 30, this impedance matching internal network 32 including fifth and sixth capacitors respectively with capacitances $C_5$, $C_6$ connected so as to form an L-shaped network, allowing matching the impedance.

Preferably, the internal integrated circuit 28 is a NFC-type circuit.

Furthermore, as illustrated in FIG. 2, a micro-storage module 31a and a voltage regulation module 31b may be disposed between the rectifier circuit 30 and the stimulator 15.

In the embodiment illustrated in FIG. 1, the value of the resistance RG is 50Ω, the resistances R20 and R24 amount to 5Ω. Moreover, the value of the first capacitance C1 is 38 pF, that of the second capacitance C2 is 62 pF, and that of the capacitance C3 is 36 pF. The value of the fourth capacitance C4 is 35 pF, that of the fifth capacitance C5 is 6.8 pF and the value of the sixth capacitance C6 is 8.2 pF. In other embodiments, the values of the different capacitances may vary slightly, yet remaining in the same order of magnitude. In this embodiment, the ratio $$\frac{C_3}{C_3 + C_4}$$

is about 0.5, which leads to a good distribution of the signal received by the internal antenna 24 between the chip 26 on the one hand and the energy recovery electronic assembly on the other hand.

In the case of the present invention, the external module 12 includes a unique external antenna 20, and the internal module 14 includes a unique internal antenna 24. Each antenna 20, 24 is both a receiver antenna and an emitter antenna. More particularly, the external antenna 20 is an energy and data emitter antenna, and, potentially, a data receiver antenna, and the internal antenna 24 is a data and energy receiver antenna and, potentially, a data emitter antenna. The external and internal antennas 20, 24 are designed so as to obtain an inductance value which allows resonating at a frequency comprised between 12 and 14 MHz, more specifically at a frequency of 13.56 MHz (so-called ISM frequency), taking account of the equivalent input impedance Z of the internal integrated circuit 28 of the chip 26.

Thanks to these two antennas 20, 24, the external module 12 and the internal module 14 transfer energy and data from one to the other simultaneously, and over a unique frequency band. In addition, as already mentioned, the external module 12 and the internal module 14 can transfer data from one to the other in a bidirectional manner.

As already indicated in the introduction, the internal integrated circuit 28 of the chip 26 has an input stage containing a protection circuit (including in particular at least one Zener diode) leading to limiting the voltage developed at the terminals of the internal antenna 24. In an alternative embodiment, the protection may be obtained by means of a cascade of conventional diodes. This limits the energy recoverable by the electrical energy recovery assembly intended to power the stimulator 15. The addition of the capacitor $C_3$ connected in series allows limiting the voltage supplied to the internal integrated circuit 28 of the chip 26 while maintaining a high voltage at the input terminal of the electrical energy recovery electronic circuit, thus allowing for a good supply of the stimulator 15 with energy.

The ratio $$\frac{C_3}{C_3 + C_4}$$

expresses the distribution of energy between the electrical energy recovery electronic assembly of and the internal integrated circuit 28 of the chip 26. In the absence of a capacitance $C_3$, the ratio is zero and the energy transfers are very limited.

It has been observed that for a ratio $$\frac{C_3}{C_3 + C_4}$$

greater than 0.1, the energy transfer is significantly improved. Preferably, the ratio $$\frac{C_3}{C_3 + C_4}$$

is greater than 0.25, or even greater than 0.3. Preferably, the ratio $$\frac{C_3}{C_3 + C_4}$$

is less than 0.9, or even less than 0.7. If the ratio tends towards 0 ($C_3$ is small compared to $C_4$), everything happens as if there were no longer a capacitive divider bridge and the Zener diode of the internal integrated circuit 28 of the chip 26 starts limiting the input voltage of the electrical energy recovery circuit. Otherwise, for a ratio tending towards 1 ($C_3$ is high compared to $C_4$), the internal integrated circuit 28 of the chip 26 no longer receives a signal and all is transferred to the energy recovery circuit, according to:

$$V_{nfc} = \frac{C_3}{(C_3 + C_4)} * V_{antenne}$$

A maximum energy transfer is typically looked for in inductive chargers, but is not desirable in the context of an implantable device for which the transferable energy is limited by the sensitivity of the tissues and for which the intensity of the signal—transmitted at the same time as energy—should be sufficient to be properly received.

In one embodiment, the ratio $$\frac{C_3}{C_3 + C_4}$$

is comprised between 0.3 and 0.6.

In this configuration, from the electrical energy recovery electronic assembly point of view, the internal integrated circuit 28 of the chip 26 is considered as a capacitor in parallel with a variable resistor whose value depends on the input voltage, so as to model the Zener effect of a real NFC circuit for example, forming part of the impedance matching network between the internal antenna 24 and the electrical energy recovery electronic assembly.

Thus, in the present invention, the assembly formed by the third capacitor $C_3$, the internal integrated circuit 28 of the chip 26 and the internal impedance matching network 32 ensures both:

the impedance matching to optimise coupling between the internal antenna 24 and the electrical energy recovery electronic assembly, the diversion of part of the received energy, so as to ensure a stable and sufficient energy supply for the electrical energy recovery electronic assembly without affecting the operation of the chip 26.

Thus, the particularity of the transcutaneous link of the present invention is to simultaneously transfer energy and data (the data being further transferred in a bidirectional manner) by one single and the same near-field link, and therefore one single and the same antenna on each side of the skin of the subject, while recovering an optimised amount of energy at the internal module 14.

Compared to the prior art, the advantages of the present invention are:

the energy transfer is performed at the same time as the communication, with no mutual constraints, the device 10 includes only one single set of antennas 20, 24, namely one single antenna on each side of the skin of the subject, avoiding the use of several antennas and thus greatly reducing the steric hindrance, the energy and the data are transmitted over one single and the same frequency band, the device 10 is compatible with a standard NFC reading system, the range of the data transfer is reduced, contributing in limiting the risks of eavesdropping and intrusion and thus guaranteeing better transmission security.

In particular, using only one set of antennas 20, 24 allows reconciling the exchange of information and energy, which represents a change with the prior art: indeed, the devices conventionally include two separate systems (one for information, the other for energy) while the approach of the present invention allows merging the two, thereby actually reducing the bulk. This result is obtained without complicating the device since it is only a matter of adding a few passive components.

Several implants of the prior art include only one antenna, nonetheless, said antennas do not operate in this frequency band and not NFC (HF at 13.56 MHz, according to the standards ISO 14443 or ISO 15693) with energy recovery.

The device 10 according to the invention allows implementing a method for the transcutaneous transfer of energy and data wherein the voltage supplied to the internal integrated circuit 28 is comprised between 100 mV and 5 V, and the voltage supplied to the energy recovery electronic assembly is comprised between 100 mV and 50 V. Thus, the efficiency of energy transfer between the external module 12 and the internal module 14 is comprised between 10% and 70%. Moreover, the transfer rate between the external module 12 and the internal module 14 is comprised between 6 kbit/s and 900 kbit/s, preferably between 106 kbit/s and 847 kbit/s or between 6.62 kbit/s and 26.48 kbit/s, so as to also cover the standard ISO/IEC 15693.

Hence, the essential point of the present invention lies in increasing the efficiency of transcutaneous energy transfer by associating an integrated circuit, for example a standard NFC chip, with an energy recovery electronic assembly external to the integrated circuit, so as to obtain a device 10 which combines a good energy transfer efficiency with a reliable wireless communication link.

The invention claimed is:

1. An active implantable medical device able to be partially implanted in a subject, the medical device comprising, once implanted, an external module outside the subject and an internal module inside the subject, the external module and the internal module being intended to transfer data from one to the other and transfer energy from the external module to the internal module, the external module including an external antenna; and the internal module including:

an internal antenna defining two terminals, an association in series between the two terminals of an internal integrated circuit associated with the internal antenna having an equivalent input impedance with a capacitive part C4 and a capacitor with a capacitance C3 with the ratio $$\frac{c_3}{c_3 + c_4}$$

greater than or equal to 0.1, and an electrical energy recovery electronic assembly connected to the two terminals, the electrical energy recovery electronic assembly being external to the internal integrated circuit.

2. The active implantable medical device according to claim 1, wherein the ratio $$\frac{C_3}{C_3 + C_4}$$

is greater than or equal to 0.23.

3. The active implantable medical device according to claim 1, wherein the ratio $$\frac{C_3}{C_3 + C_4}$$

is comprised between 0.3 and 0.6.

4. The active implantable medical device according to claim 1, wherein the external module includes a unique external antenna, and the internal module includes a unique internal antenna.

5. The active implantable medical device according to claim 1, wherein each antenna is connected to an impedance matching circuit, and each antenna and its associated impedance matching circuit resonate at a frequency comprised between 12 and 14 MHZ, more specifically 13.56 MHz.

6. The active implantable medical device according to claim 1, wherein the external module and the internal module are intended to transfer energy and data from one to the other simultaneously.

7. The active implantable medical device according to claim 1, wherein the external module and the internal module are intended to transfer data from one to the other in a bidirectional manner.

8. The active implantable medical device according to claim 1, wherein the external module and the internal module are intended to transfer energy and data from one to the other over a unique frequency band.

9. A method for transferring energy and data, the method being implemented by means of an active implantable medical device according to claim 1, a voltage supplied to the internal integrated circuit being comprised between 100 mV and 5 V, another voltage supplied to the electrical energy recovery electronic assembly being comprised between 100 mV and 50 V.

10. The method for transferring energy and data according to claim 9, wherein the transfer rate between the external module and the internal module is comprised between 6 kbit/s and 900 kbit/s.

11. The method for transferring energy and data according to claim 9, wherein the transfer rate between the external module and the internal module is comprised between 106 kbit/s and 847 kbit/s or between 6.62 kbit/s and 26.48 kbit/s.

12. The method for transferring energy and data according to claim 9, wherein the efficiency of energy transfer between the external module and the internal module is comprised between 10% and 70%.

13. The method for transferring energy and data according to claim 9, wherein the transfer rate between the external module and the internal module is comprised between 6 kbit/s and 900 kbit/s, and the efficiency of energy transfer between the external module and the internal module is comprised between 10% and 70%.

14. The method for transferring energy and data according to claim 9, wherein the transfer rate between the external module and the internal module is comprised between 106 kbit/s and 847 kbit/s or between 6.62 kbit/s and 26.48 kbit/s.

* * * * *